(12) United States Patent
Bratovanov et al.

(10) Patent No.: US 8,080,663 B2
(45) Date of Patent: Dec. 20, 2011

(54) PROCESS FOR THE PREPARATION OF 2-METHYLSPIRO(1,3-OXATHIOLANE-5,3')QUINICLIDINE

(75) Inventors: Svetoslav S. Bratovanov, Ancaster (CA); Elena Bejan, Brantford (CA); Zhi-Xian Wang, Brantford (CA); Stephen E. Horne, Burlington (CA)

(73) Assignee: Apotex Pharmachem Inc, Braniford (CA)

( * ) Notice: Subject to any disclaimer, the term of this patent is extended or adjusted under 35 U.S.C. 154(b) by 953 days.

(21) Appl. No.: 11/730,770

(22) Filed: Apr. 4, 2007

(65) Prior Publication Data

US 2008/0249312 A1   Oct. 9, 2008

(51) Int. Cl.
*C07D 453/02* (2006.01)
(52) U.S. Cl. ....................................... 546/137
(58) Field of Classification Search ............ 546/137
See application file for complete search history.

(56) References Cited

U.S. PATENT DOCUMENTS

| 4,855,290 A | 8/1989 | Fisher |
| 4,861,886 A | 8/1989 | Haga |
| 5,571,918 A | 11/1996 | Hayashi |

OTHER PUBLICATIONS http://medical-dictionary.thefreedictionary.com/aryl (2010).*
Sigma-Aldrich Chemical Catalog, on-line structure search (2010).*
Bos M., EPC-Synthesis of (S)-3-Hydroxy-3-Mercaptomethyl-Quinuclidine, A Chiral Building Block for the Synthesis of the Muscarinic . . . , Heterocycles; 1994;38(8):1889-1896.
Sorbera L.A., Cevimeline Hydrochloride; Drugs of the Future; 2000;25 (6):558-562.

* cited by examiner

*Primary Examiner* — Rita Desai
*Assistant Examiner* — John Mabry

(57) ABSTRACT

An industrially acceptable process for the preparation of 2-methylspiro(1,3-oxathiolane-5,3')quiniclidine. The cis-isomer of 2-methylspiro(1,3-oxathiolane-5,3')quiniclidine is known generally as Cevimeline.

6 Claims, No Drawings

PROCESS FOR THE PREPARATION OF 2-METHYLSPIRO(1,3-OXATHIOLANE-5,3')QUINICLIDINE

FIELD OF THE INVENTION

The invention generally relates to an industrially acceptable process for the preparation of 2-methylspiro(1,3-oxathiolane-5,3')quiniclidine. The cis-isomer of 2-methylspiro(1,3-oxathiolane-5,3')quiniclidine is known generally as Cevimeline.

BACKGROUND OF THE INVENTION

The present invention refers to a novel, industrially advantageous process for the preparation of an intermediate useful for the preparation of Cevimeline hydrochloride (1, cis-2-methylspiro(1,3-oxathiolane-5,3')quiniclidine, Scheme 1). This pharmaceutical is useful for the treatment of diseases of the central nervous system due to disturbances of central cholinergic function and autoimmune system (Sjörgen's syndrome) and is marketed as Evoxac®.

U.S. Pat. No. 4,855,290 describes a process for preparation of 2-methylspiro(1,3-oxathiolane-5,3')quiniclidine (1). The process comprises the preparation of the epoxide of 3-methylenequiniclidine, which is subsequently reacted with hydrogen sulfide to produce 3-hydroxy-3-mercaptomethylquiniclidine and condensed with acetaldehyde in the presence of a Lewis acid (boron trifluoride etherate) to provide 2-methylspiro(1,3-oxathiolane-5,3')quiniclidine. This process is depicted in Scheme I.

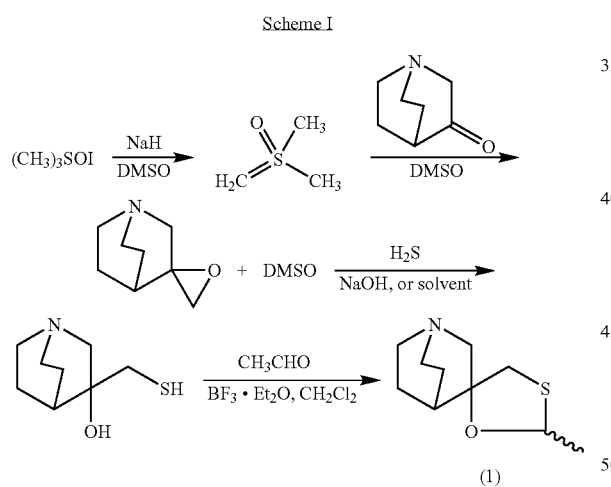

This process suffers from major disadvantages when transiting to industrial scale. These include the use of the highly hazardous and difficult to handle hydrogen sulfide gas. Also, boron trifluoride etherate is employed during the condensation step with acetaldehyde. The boron trifluoride etherate reagent is an air and moisture sensitive Lewis acid which has to be used under anhydrous conditions, thus creating a serious disadvantage in industrial settings. Another drawback of this process is the use of sodium hydride. U.S. Pat. Nos. 5,571,918 and 4,861,886 relate to the isomerization of the trans- to cis-form of 2-methylspiro(1,3-oxathiolane-5,3')quiniclidine but do not describe methods for its preparation. Thus, an industrially acceptable and cost-effective method for the preparation of Cevimeline hydrochloride which overcomes the deficiencies of the prior art is required.

Further and other objects of the invention will be realized by those skilled in the art from the following Summary of the Invention and Detailed Description of Preferred Embodiments of the Invention thereof.

SUMMARY OF THE INVENTION

The present invention provides a novel process for the preparation of 2-methylspiro(1,3-oxathiolane-5,3')quiniclidine (1) involving a concise and robust four step, two-pot sequence. This route has many desirable attributes relative to the prior art methods such as avoiding the use of hydrogen sulfide gas by using the industrially more acceptable and inexpensive thiolacetic acid. Overall, the advantages of the instant invention result in a new synthetic process to produce 2-methylspiro(1,3-oxathiolane-5,3')quiniclidine in an efficient, safer and environmentally friendlier manner.

DESCRIPTION OF PREFERRED EMBODIMENTS OF THE INVENTION

According to one aspect of the invention, a novel process is provided for the preparation of 2-methylspiro(1,3-oxathiolane-5,3')quiniclidine (1). The process is industrially practical, efficient, safe and economical, as well as being environmentally friendly. The general method is shown in the Scheme II.

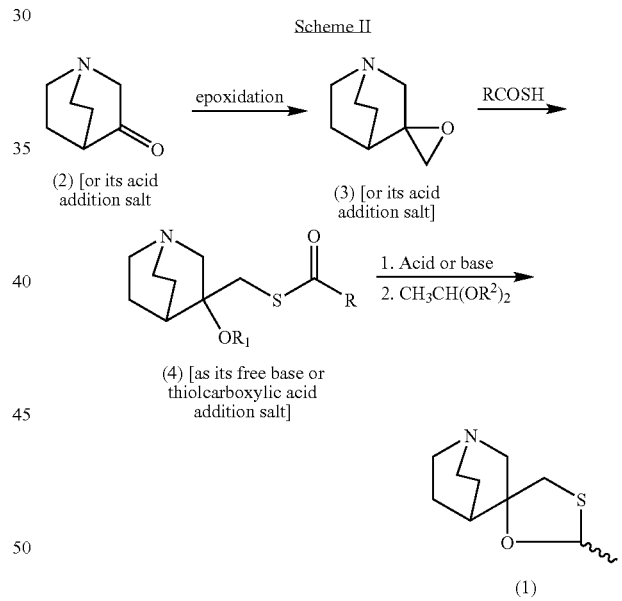

wherein R is selected from C1 to C6 alkyl and aryl groups, most preferably a methyl, ethyl or propyl group; $R^1$ is hydrogen or a C2 to C7 alkyl or aryl carbonyl group; $R^2$ is a C1 to C6 alkyl group, preferably methyl, ethyl, propyl, or butyl group.

The first step, as shown in Scheme II, involved the preparation of the epoxide of 3-methylenequiniclidine (3) by any method known in the art. An example of a preferred method was modification of Corey's epoxidation method with dimethylsulfoxonium methylide, which can be prepared from a trimethylsulfoxonium salt, such as trimethylsulfoxonium chloride, trimethylsulfoxonium bromide, trimethylsulfoxonium iodide, trimethylsulfoxonium methanesulfonate, trimethylsulfoxonium tosylate, trimethylsulfoxonium tetrafluoroborate or trimethylsulfoxonium triflate, and a base or a mixture of bases. In this case, the sodium hydride, traditionally used in this procedure, was preferably substituted with an industrially more acceptable base, such as sodium tert-butoxide, potassium tert-butoxide and the like. Using this modification, the reaction proceeded under mild conditions and in a good yield. The dimethylsulfoxonium methylide can be pre-prepared or prepared in situ during the reaction. Typically, the solution of the base in the solvent was added to the mixture of 3-quinuclidinone or its acid addition salt and trimethylsulfoxonium salt in a polar organic solvent, for instance a C3-C6 cyclic or acyclic sulfoxide or sulfone such as dimethylsulfoxide or sulfolane. The temperature during the addition was between about 0° C. and about 20° C. After the reaction was complete, the product was isolated, for instance, from the mixture by extraction with an organic solvent selected from a C1 to C6 alkyl, a C6 to C9 aryl, a C7 to C10 aralkyl, a C4 to C10 alkyl ester, a C2 to C4 halogenated alkyl or mixtures thereof. Examples of preferred solvents include ethyl acetate, isopropyl acetate, heptane and toluene or 1-chlorobutane. Most preferably the solvent is toluene. This provides, after evaporation, the product in about 50 to about 80% yield. In a preferred embodiment of the invention, the organic extract of the product could be used in the next step without further purification or isolation of the product. In the next step of the invention the epoxide (3) was reacted with a thiolcarboxylic acid RCOSH to provide compound (4). R is selected from C1 to C6 alkyl and aryl groups, most preferably a methyl, ethyl or propyl group. The reaction is carried out in the presence of an organic solvent at a temperature between −20° C. to 100° C., preferably between 0° C. to 50° C. Examples of suitable organic solvents include a C1 to C6 alkyl, a C6 to C9 aryl, a C7 to C10 aralkyl, a C4 to C10 alkyl ester, or mixtures thereof. Most preferably the solvent is toluene. The product may be isolated as its free base form or salt form, and preferably its thiolcarboxylic acid addition salt form. During this step a precipitate forms spontaneously that can be easily separated from the reaction mixture by filtration. The product thus obtained, in about 70% to about 90% yield, is the thiolcarboxylic acid salt of 3-hydroxy-3-alkylcarboxymercaptomethylquinuclidine (4, $R^1$=H) or 3-alkylcarboxy-3-alkylcarboxymercaptomethylquinuclidine (4, $R^1$=C2 to C7 alkyl or aryl carbonyl group) or the mixture thereof having sufficient purity for use in the next step without further purification.

The final step in Scheme II involves two chemical reactions and they are detailed in Scheme III. The first reaction converts compound (4) or its salt into an intermediate 3-hydroxy-3-mercaptomethylquinuclidine (5). The conversion may be carried out in the presence of acid or base. Suitable acids include inorganic acids such as hydrochloric acid, sulfuric acid, perchloric acid, and organic acids such as methanesulfonic acid, p-toluenesulfonic acid, benzenesulfonic acid. The suitable bases include alkali metal hydroxides such as sodium hydroxide, potassium hydroxide, and lithium hydroxide; alkali metal carbonates such as sodium carbonate, potassium carbonate and lithium carbonate; and alkali alkylates such sodium methoxide, sodium ethoxide, sodium tert-butoxide and the like. The intermediate (5) can be isolated or can be carried into the next step without isolation (one-pot sequence). The one-pot sequence is preferable because it employs less solvent, permits reduced process cycle times and furnishes improved yields. In the one pot sequence, compound (4) in a C1 to C6 alcoholic solvent, for instance iso-propanol, methanol, butanol, or mixtures thereof, is contacted with an acid. Various types of acids could be used including inorganic acids, organic sulfonic acids, most preferably p-toluenesulfonic acid and benzenesulfonic acid. This reaction is performed at temperatures between 40° C. and 130° C., to produce 3-hydroxy-3-mercaptomethylquinuclidine (Scheme III). Addition of acetaldehyde dialkyl acetal to the mixture and additional stirring at temperatures between about 40° C. and about 130° C. produces a cis/trans mixture of 2-methylspiro(1,3-oxathiolane-5,3')quinuclidine in cis/trans ratios from about 1:1 to about 10:1 (cis- and trans-1). The present invention allows the preparation of a high proportion of the cis-isomer of 2-methylspiro(1,3-oxathiolane-5,3')quinuclidine in an one-pot sequence, directly from the reaction of compound 4 with an acid or a base followed by the subsequent condensation of the obtained intermediate with acetaldehyde dialkyl acetal. The process described by this invention is industrially advantageous and cost-efficient as minimum purification and separation steps of the cis-isomer will be required to achieve the requisite specifications for use as an active pharmaceutical ingredient.

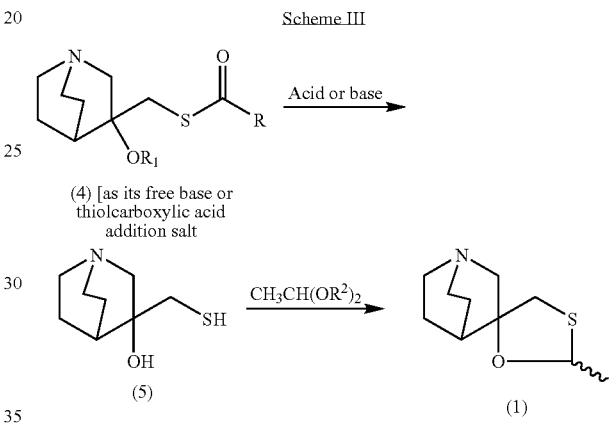

Scheme III (4) [as its free base or thiolcarboxylic acid addition salt]

Overall, the new process depicted in Schemes II and Scheme III consists of four high-yielding chemical transformations. The main advantage relative to the previously reported process includes the use of thiolcarboxylic acid instead of the toxic and hazardous hydrogen sulfide. The other advantage is that the four steps can be conducted with the isolation of only one intermediate: compound (4). This new process is robust, efficient and provides a cis/trans mixture of 2-methylspiro(1,3-oxathiolane-5,3')quinuclidine enriched in favor of the cis-isomer, which is the active ingredient of Cevimeline hydrochloride.

The following examples are merely representative of the present invention and are not intended to be limiting.

EXAMPLE I

Preparation of the Epoxide of 3-methylenequinuclidine (3)

A mixture of the hydrochloric salt of 3-quinuclidinone (2, 120 g, 795.7 mmol) and trimethylsulfoxonium iodide (219 g, 993.3 mmol) in dimethylsulfoxide (91.0 g, 0.63 mol) was cooled to 0-5° C. in an ice/water bath under nitrogen atmosphere. A solution of potassium tert-butoxide (201 g, 1789.1 mmol) in dimethylsulfoxide (500 mL) was added dropwise over 45 minutes. The mixture was warmed gradually to room temperature and stirred for an additional 16 hours at room temperature. After cooling to 0-5° C. (ice/water bath) the mixture was poured into an ice/water mixture (500 g) and then sodium chloride (300 g) was added. The mixture was stirred for 30 minutes and extracted with toluene (3×400 mL).

The toluene phase was dried over sodium sulfate, filtered and evaporated to furnish the epoxide of 3-methylenequiniclidine (60 g, 431.7 mmol, 54% yield) as a yellow oil. The product could be used in the next step neat or as toluene solution after the extraction without further purification.

$^1$H NMR (400 MHz, CDCl$_3$): δ=3.10 (d, 1H, J=14.6 Hz); 2.98-2.77 (m, 5H); 2.74 (d, 1H, J=4.8 Hz); 2.70 (d, 1H, J=4.8 Hz); 1.96-1.89 (m, 1H); 1.79-1.62 (m, 2H); 1.60-1.54 (m, 1H); 1.38-1.36 (m,1H).

LRMS (ES+): 140.0 (100, M+H$^+$).

EXAMPLE II

Preparation of the Thiolacetic Acid Salt of 3-hydroxy-3-acetoxymercaptomethylquiniclidine (4)

A solution of the epoxide of 3-methylenequiniclidine (3, 54 g, 388.5 mmol) in toluene (200 mL) was cooled to 0-5° C. (ice/water bath). Thiolacetic acid was added dropwise over 10-15 minutes. The mixture was stirred at 0-5° C. for 30 minutes and then allowed to come to room temperature. After stirring at room temperature for 2 hours the formed precipitate was filtered and washed with toluene (2×100 mL) to give the 3-hydroxy-3-acetoxymercaptomethylquiniclidine thiolacetic acid salt (4 wherein R$^1$ is H and R is methyl, 77 g, 264.6 mmol, 68%) as a light yellow solid. The product was used in the next step without any further purification.

$^1$H NMR (400 MHz CD$_3$OD): δ=3.47 (d, 1H, J=14.1 Hz); 3.37-3.18 (m, 7H); 2.40 (s, 3H); 2.38 (s, 3H); 2.36-2.27 (m, 1H), 2.14-2.05 (m, 2H); 2.03-1.93 (m, 1H); 1.81-1.78 (m, 1H).

LRMS (ES+): 216.1 (100, M−[SCOCH$_3$]$^-$+H$^+$).

EXAMPLE III

Preparation of 2-methylspiro(1,3-oxathiolane-5,3') quiniclidine using p-toluenesulfonic acid (1)

To a solution of 3-hydroxy-3-acetoxymercaptomethylquiniclidine thiolacetic acid salt (4 wherein R$^1$ is H and R is methyl, 3 g, 10.3 mmol) in iso-propanol (50 mL) was added p-toluenesulfonic acid monohydrate (5.9 g, 30.9 mmol) and the mixture was heated to reflux for 3.5 hours. The mixture was cooled to room temperature and acetaldehyde diethyl acetal (6.1 g, 51.5 mmol) was added. The mixture was heated to reflux and stirred for an additional 3 hours. The solvent was evaporated and the residue was dissolved in dichloromethane (50 mL). The mixture was cooled to 0-5° C. and a 25% aqueous solution of sodium hydroxide (80 mL) was added. The mixture was stirred for 10-15 minutes and the phases were separated. The aqueous phase was extracted with dichloromethane (3×50 mL). The organic phases were combined and extracted with 5% aqueous solution of sulfuric acid (3×50 mL). The acidic aqueous phases were combined and the pH was adjusted to 12 with a 25% aqueous solution of sodium hydroxide. The aqueous phase was extracted with heptane (3×50 mL) and the organic phases were combined, dried over sodium sulfate and the solvent was evaporated to give 2-methylspiro(1,3-oxathiolane-5,3')quiniclidine (1.8 g, 9.2 mmol, 89% yield) as a 3:1 cis/trans ratio mixture of diastereomers (determined by $^1$H NMR).

LRMS (ES+): 200.1 (100, M+H$^+$).

EXAMPLE IV

Preparation of 2-methylspiro(1,3-oxathiolane-5,3') quiniclidine (1) using racemic camphorsulfonic acid In a similar experiment as Example III, racemic camphorsulfonic acid (7.2 g, 30.9 mmol) was added to a solution of 3-hydroxy-3-acetoxymercaptomethylquiniclidine thiolacetic acid salt (4 wherein R$^1$ is H and R is methyl, 3 g, 10.3 mmol) in iso-propanol (50 mL). The mixture was refluxed for 5 h, cooled to room temperature and acetaldehyde diethyl acetal (6.1 g, 51.5 mmol) was added. The mixture was refluxed for an additional an 8 hours and processed according to Example III to give 2-methylspiro(1,3-oxathiolane-5,3') quiniclidine (1.32 g, 6.63 mmol, 64% yield) in a 3.5:1 cis/trans ratio mixture of diastereomers (determined by $^1$H NMR).

EXAMPLE V

Preparation of 2-methylspiro(1,3-oxathiolane-5,3') quiniclidine (1) using phenyl sulfonic acid In a similar experiment as Example III, to a solution of 3-hydroxy-3-acetoxymercaptomethylquiniclidine thiolacetic acid salt (4 wherein R$^1$ is H and R is methyl, 3 g, 10.3 mmol) in iso-propanol (50 mL) was added phenyl sulfonic acid (4.9 g, 30.9 mmol) and the mixture was refluxed 5 h, cooled to room temperature and acetaldehyde diethyl acetal (6.1 g, 51.5 mmol) was added. The mixture was refluxed for an additional 8 hours and worked up in a manner similar to Example III to furnish 2-methylspiro(1,3-oxathiolane-5,3') quiniclidine (1.6 g, 8.2 mmol, 80% yield) as a 2.5:1 cis/trans ratio mixture of diastereomers (determined by $^1$H NMR).

EXAMPLE VI

Preparation of 2-methylspiro(1,3-oxathiolane-5,3') quiniclidine (1) using p-toluenesulfonic acid in butanol To a solution of 3-hydroxy-3-acetoxymercaptomethylquiniclidine thiolacetic acid salt (4 wherein R$^1$ is H and R is methyl, 3 g, 10.3 mmol) in butanol (100 mL) was added of p-toluenesulfonic acid monohydrate (5.9 g, 30.9 mmol) and the mixture was refluxed for 3 hours with a Dean-Stark apparatus attached to the flask. The reaction mixture was cooled to room temperature and acetaldehyde diethyl acetal (6.1 g, 51.5 mmol) was added. The mixture was heated to 80° C. for an additional 8 h and worked up according to Example III to afford 2-methylspiro(1,3-oxathiolane-5,3')quiniclidine (1.8 g, 9.2 mmol, 89% yield) as a 3:1 cis/trans ratio mixture of diastereomers (determined by $^1$H NMR).

While the foregoing provides a detailed description of a preferred embodiment of the invention, it is to be understood that this description is illustrative only of the principles of the invention and not limitative. Furthermore, as many changes can be made to the invention without departing from the scope of the invention, it is intended that all material contained herein be interpreted as illustrative of the invention and not in a limiting sense.

The invention of claimed is:
1. 3-Hydroxy-3-acetoxymercaptomethylquiniclidine.
2. 3-Acetoxy-3-acetoxymercaptomethylquiniclidine.
3. A compound of formula (4):

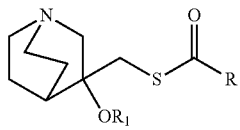

(4)

wherein
R is selected from the group consisting of C1 to C6 alkyl and phenyl ; and
$R^1$ is hydrogen.
4. A thiolacetic acid salt of the compound of claim 1.
5. A thioacetic acid salt of the compound of claim 2.
6. A thiolcarboxylic acid addition salt of the compound of claim 3.

* * * * *